US005650433A

United States Patent [19]
Watanabe et al.

[11] Patent Number: 5,650,433
[45] Date of Patent: Jul. 22, 1997

[54] CHONDROPROTECTIVE AGENTS

[75] Inventors: Koju Watanabe; Koichi Niimura, both of Saitama; Kiyonori Umekawa, Chiba, all of Japan

[73] Assignee: Kureha Chemical Industry Co., Ltd., Tokyo, Japan

[21] Appl. No.: 519,179

[22] Filed: Aug. 25, 1995

Related U.S. Application Data

[63] Continuation of Ser. No. 271,951, Jul. 8, 1994, abandoned.

[30] Foreign Application Priority Data

Jul. 9, 1993 [JP] Japan ..................... 5-194182

[51] Int. Cl.$^6$ .................................................. A61K 31/35
[52] U.S. Cl. ........................................... 514/456; 514/453
[58] Field of Search ..................... 544/151; 424/248, 424/261; 514/456, 453

[56] References Cited

U.S. PATENT DOCUMENTS

| 4,268,517 | 5/1981 | Niebes et al. | 424/283 |
| 4,944,949 | 7/1990 | Story et al. | 424/451 |

FOREIGN PATENT DOCUMENTS

| 0395441 | 10/1990 | European Pat. Off. . |
| 2811695A | 9/1979 | Germany . |

OTHER PUBLICATIONS

Agents and Actions, vol. 12, No. 3, 1982, (pp. 298–302); O.P. Agarwal 'The anti–inflammatory action of nepitrin, a flavonoid'.

Chem. Pharm. Bull. vol. 32, No. 7, 1984, (pp. 2724–2729); M. Kubo et al 'Studies on scutellariae radix. VII Anti–arthritic and anti–inflammatory actions of methanolic extract and flavonoid components from scutellariae radix'.

Arch. Pharm Res., vol. 16, No. 1, 1993, (pp. 25–28; S.J. Lee et al "antiinflammatory activity of naturally occurring flavone and flavonon glycosides".

Fitoterapia, vol. 90 No. 5, 1990, (pp. 460–461); G.B.S. Reddy et al "comparison of the anti–inflammatory activity of certain methoxyflavonoids".

Indian J. Pharmacol. Sci., vol. 55 No. 5, Sep. 1993 (pp. 180–183); N.S. Muthia et al 'Anti–infammatory activity of flavone and its methoxy derivatives—a structure activity study'.

*Primary Examiner*—Elli Peselev
*Attorney, Agent, or Firm*—Sughrue, Mion, Zinn, Macpeak & Seas

[57] ABSTRACT

A chondroprotective agent comprising a flavonoid compound of the general formula (I):

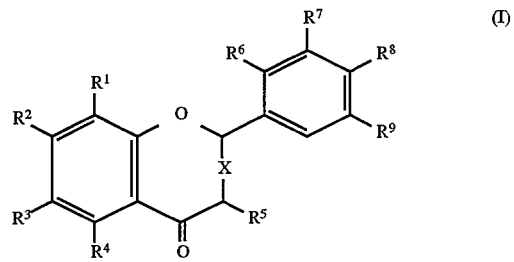

wherein $R^1$ to $R^9$ are, independently, a hydrogen atom, hydroxyl group, or methoxyl group and X is a single bond or a double bond, or a stereoisomer thereof, or a naturally occurring glycoside thereof is disclosed. The above compound strongly inhibits proteoglycan depletion from the chondrocyte matrix and exhibits a function to protect cartilage, and thus, is extremely effective for the treatment of arthropathy.

11 Claims, No Drawings

CHONDROPROTECTIVE AGENTS

This is a continuation of application Ser. No. 08/271,951 filed Jul. 8, 1994 now abandoned.

BACKGROUND OF THE INVENTION

1. Field of the Invention

The present invention relates to an agent for protecting cartilage, i.e., a chondroprotective agent, more particularly, a chondroprotective agent containing a flavonoid compound or a stereoisomer thereof, or a naturally occurring glycoside thereof.

2. Description of the Related Art

There are various types of arthropathy, for example, rheumatoid arthritis, rheumatic fever, and osteoarthritis. Many people particularly suffer from rhematoid arthritis and osteoarthritis. These diseases have been studied as the major types of arthropathy. There are congenital and secondary osteoarthritis, and further primary osteoarthritis caused by degeneration of the articular cartilage along with aging. Patients suffering from primary osteoarthritis have recently been increasing along with the increase in the population of the aged.

Although there are considerable differences of the causes and conditions between rheumatoid arthritis and osteoarthritis, the articular function becomes eventually obstructed by the destruction of the cartilage in both of rheumatoid arthritis and osteoarthritis.

The first choice of medicines for the treatment of rheumatic diseases such as rheumatoid arthritis, rheumatic fever, systemic lupus erythematosus, and osteoarthritis are analgesic and anti-inflammatory agents, for example, aspirin or indometacin. Further, gold compounds such as Shiosol, immunomodulators, steroids, or D-penicillamine are used as medicines for the treatment of rheumatoid arthritis.

The above conventional analgesic and anti-inflammatory agents, however, were not effective against the destruction of the articular cartilage, and in fact, sometimes exhibited adverse effect in experiments using chondrocytes. Further, no inhibitory effect on articular cartilage destruction was also observed in the above-mentioned medicines for the treatment of rheumatoid arthritis.

It is known that flavonoids may be used as an agent for protecting a blood vessel and further in the following pharmaceutical applications: a virus genome deactivating agent for apigenin, chrysin, morin, fisetin, and baicalein [Japanese Unexamined Patent Publication (Kokai) No. 2-101013], an agent for determining the function of polymorphonuclear leukocyte for flavonoids [Japanese Unexamined Patent Publication (Kokai) No. 63-253254], an oral agent for suppressing smoking for flavonoids [Japanese Unexamined Patent Publication (Kokai) No. 4-46119], treatment of high protein edema for rutin, diosmin, and the like (U.S. Pat. No. 5,096,887), an anti-tumor agent containing flavonoids [Japanese Unexamined Patent Publication (Kokai) No. 3-275625], an anti-tumor agent containing apigenin [Japanese Examined Patent Publication (Kokoku) No. 3-61644], an agent for suppressing the formation of peroxylipid for hespererin, kaempferol, and the like [Japanese Unexamined Patent Publication (Kokai) No. 3-5423], an anti-tumor agent containing kaempferol [Japanese Unexamined Patent Publications (Kokai) No. 4-103529 and No. 4-103532], a calcium antagonist for hesperidin and luteolin [Japanese Unexamined Patent Publication (Kokai) No. 4-243822], a sialidase inhibitor for luteolin [Japanese Unexamined Patent Publication (Kokai) No. 64-42427], an anti-retrovirus agent for luteolin [Japanese Unexamined Patent Publication (Kokai) No. 3-7224], an anti-HBV (hepatitus B virus) agent for quercetin [Japanese Unexamined Patent Publication (Kokai) No. 4-234320], and the like.

Flavonoids have not, however, been known to be useful as chondroprotective agents.

SUMMARY OF THE INVENTION

The present inventors engaged in intensive research to develop a chondroprotective agent for suppressing the destruction of the articular cartilage and as a result found that the particular flavonoid compounds and stereoisomers thereof, and the naturally occurring known glycosides thereof showed significant inhibition of the depletion of proteoglycan which is a major component of the cartilage matrix, and therefore, are useful as a chondroprotective agent for prohibiting the destruction of the articular cartilage.

Accordingly, the object of the present invention is to provide a chondroprotective agent containing as an active ingredient a particular flavonoid compound or a stereoisomer thereof, or a naturally occurring known glycoside thereof.

Other objects and effects of the present invention will be clear from the following description.

The present invention relates to a chondroprotective agent comprising a flavonoid compound of the general formula (I):

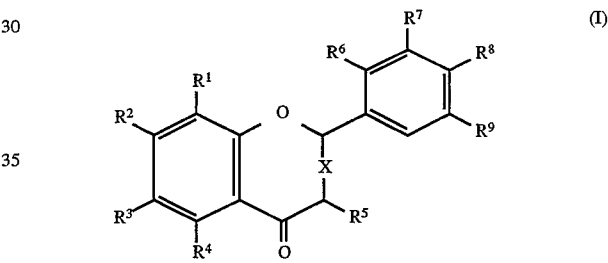

wherein $R^1$ to $R^9$ are, independently, a hydrogen atom, hydroxyl group, or methoxyl group and X is a single bond or a double bond, or a stereoisomer thereof, or a naturally occurring glycoside thereof (hereinafter referred to as "the present substance").

DETAILED DESCRIPTION OF THE PREFERRED EMBODIMENTS

The active ingredient of the chondroprotective agent according to the present invention is a flavonoid, which is widely present in the vegetable kingdom. Typical flavonoid compounds include flavones, flavonols, flavanones, and flavanonols. Flavanones contain an asymmetric carbon atom at the 2-position, and flavanonols contain asymmetric carbon atoms at the 2- and 3-positions, and such compounds may be present as the stereoisomers. These stereoisomers can also be used in the present invention. Further, the saccharides present in the above naturally occurring glycosides are not particularly limited. As examples of the naturally occurring glycosides, there may be mentioned glucoside, galactoside, fructoside, rhamnoside, rutinoside (that is, rhamnoglucoside), arabinoside, xyloside, apioglucoside, and robinobioside.

In the present invention, any naturally occurring flavonoids may be used as the above present substance. The flavonoid compounds and naturally occurring glycosides thereof shown in the following Table 1 are preferable.

TABLE 1

| No. | Name | $R^1$ | $R^2$ | $R^3$ | $R^4$ | $R^5$ | $R^6$ | $R^7$ | $R^8$ | $R^9$ | X |
|---|---|---|---|---|---|---|---|---|---|---|---|
| 1 | Flavone | H | H | H | H | H | H | H | H | H | Double |
| 2 | Chrysin | H | OH | H | OH | H | H | H | H | H | " |
| 3 | Toringin | H | OH | H | OGlu | H | H | H | H | H | " |
| 4 | Primetin | OH | H | H | OH | H | H | H | H | H | " |
| 5 | Apigenin | H | OH | H | OH | H | H | H | OH | H | " |
| 6 | Cosmosiin | H | OGlu | H | OH | H | H | H | OH | H | " |
| 7 | Apiin | H | OApg | H | OH | H | H | H | OH | H | " |
| 8 | Luteolin | H | OH | H | OH | H | H | OH | OH | H | " |
| 9 | Galuteolin | H | OH | H | OGlu | H | H | OH | OH | H | " |
| 10 | Gluco-luteolin | H | OGlu | H | OH | H | H | OH | OH | H | " |
| 11 | Acacetin | H | OH | H | OH | H | H | H | $OCH_3$ | H | " |
| 12 | Linarin | H | ORut | H | OH | H | H | H | $OCH_3$ | H | " |
| 13 | Diosmetin | H | OH | H | OH | H | H | OH | $OCH_3$ | H | " |
| 14 | Diosmin | H | ORut | H | OH | H | H | OH | $OCH_3$ | H | " |
| 15 | Baicalein | H | OH | OH | OH | H | H | H | H | H | " |
| 16 | Fisetin | H | OH | H | H | OH | H | H | OH | H | " |
| 17 | Kaempferol | H | OH | H | OH | OH | H | H | OH | H | " |
| 18 | Trifolin | H | OH | H | OH | OGal | H | H | OH | H | " |
| 19 | Astragalin | H | OH | H | OH | OGlu | H | H | OH | H | " |
| 20 | Robinin | H | ORha | H | OH | ORob | H | H | OH | H | " |
| 21 | Kaempferitrin | H | ORha | H | OH | ORha | H | H | OH | H | " |
| 22 | Quercetin | H | OH | H | OH | OH | H | OH | OH | H | " |
| 23 | Quercitrin | H | OH | H | OH | ORha | H | OH | OH | H | " |
| 24 | Iso-quercitrin | H | OH | H | OH | OGlu | H | OH | OH | H | " |
| 25 | Rutin | H | OH | H | OH | ORut | H | OH | OH | H | " |
| 26 | Morin | H | OH | H | OH | OH | OH | H | OH | H | " |
| 27 | Myricetin | H | OH | H | OH | OH | H | OH | OH | OH | " |
| 28 | Myricitrin | H | OH | H | OH | ORha | H | OH | OH | OH | " |
| 29 | Datiscetin | H | OH | H | OH | OH | OH | H | H | H | " |
| 30 | Quercetagetin | H | OH | OH | OH | OH | H | OH | OH | H | " |
| 31 | Quercetagitrin | H | OGlu | OH | OH | OH | H | OH | OH | H | " |
| 32 | Rhamnetin | H | $OCH_3$ | H | OH | OH | H | OH | OH | H | " |
| 33 | Iso-rhamnetin | H | OH | H | OH | OH | H | $OCH_3$ | OH | H | " |
| 34 | Pinocembrin | H | OH | H | OH | H | H | H | H | H | Single |
| 35 | Naringenin | H | OH | H | OH | H | H | H | OH | H | " |
| 36 | Salipurpin | H | OH | H | OGlu | H | H | H | OH | H | " |
| 37 | Prunin | H | OGlu | H | OH | H | H | H | OH | H | " |
| 38 | Naringin | H | ORha | H | OH | H | H | H | OH | H | " |
| 39 | Sakuranetin | H | $OCH_3$ | H | OH | H | H | H | OH | H | " |
| 40 | Sakuranin | H | $OCH_3$ | H | OGlu | H | H | H | OH | H | " |
| 41 | Hesperetin | H | OH | H | OH | H | H | OH | $OCH_3$ | H | " |
| 42 | Hesperidin | H | ORut | H | OH | H | H | OH | $OCH_3$ | H | " |
| 43 | Eriodictyol | H | OH | H | OH | H | H | OH | OH | H | " |
| 44 | Eriodictin | H | oRha | H | OH | H | H | OH | OH | H | " |
| 45 | Pinobanksin | H | OH | H | OH | OH | H | H | H | H | " |
| 46 | Aromadendrin | H | OH | H | OH | OH | H | H | OH | H | " |
| 47 | Engelitin | H | OH | H | OH | ORha | H | H | OH | H | " |
| 48 | Fustin | H | OH | H | H | OH | H | OH | OH | H | " |
| 49 | Taxifolin | H | OH | H | OH | OH | H | OH | OH | H | " |
| 50 | Astilbin | H | OH | H | OH | ORha | H | OH | OH | H | " |
| 51 | Ampelopsin | H | OH | H | OH | OH | H | OH | OH | OH | " |

OGlu: Glucoside, OApg: Apioglucoside, ORut: Rutinoside, OGal: Galactoside, oRha: Rhamnoside, ORob: Robinobioside The compounds Nos. 34 to 51 in Table 1 include a single bond as X. Thus, the carbon atom in the 2-position or the carbon atoms in the 2- and 3-positions are asymmetrical, and there exist stereoisomers. It is known that pinocembrin includes (±) and (S) isomers; naringenin, sakuranetin, hesperetin and eriodictyol include (±), (R), and (S) isomers; pinobanksin includes (2R-trans) and (2S-trans) isomers; aromadendrin and fustin include trans-(±), (2R-trans), and (2S-trans) isomers; taxifolin and ampelopsin include trans-(±), (2R-trans), (2S-trans), and (2R-cis) isomers.

It is possible to use, as the flavonoids, compounds isolated and purified from naturally occurring plants or chemically synthesized. Many compounds described in Table 1 are commercially available. For example, it is possible to obtain flavone, apigenin, luteolin, acacetin, linarin, diosmetin, baicalein, fisetin, kaempferol, quercetin, hesperetin, and hesperidin from Funakoshi Co., Ltd., Tokyo.

Examples of the acute toxicity of the present substance are as follows: Mouse $LD_{50}$ of quercetin (oral administration): 160 mg/kg and mouse $LD_{50}$ of fisetin (intravenous injection): 180 mg/kg.

Further, no abnormalities were observed for a week after hespererin was administered orally to BALB/c mice (female, seven weeks old) at the dose of 100 mg/kg. The same results were obtained where hesperidin, acacetin, diosmetin, apigenin, luteolin, or kaempferol was administered.

As a pharmacological effect, the present substance exhibits the function to inhibit destruction of chondrocyte matrix in chondrocyte culture (derived from cartilage of rabbit shoulder and knee joints) (see Example 1 as below).

Accordingly, the present substance is useful as a chondroprotective agent for treating various types of arthropathy accompanying the cartilage destruction of joints. Examples of such arthropathy are rheumatoid arthritis, osteoarthritis, periarthritis humeroscapularis, shoulder-arm-neck syndrome, lumbago, etc.

The chondroprotective agent containing the present substance as an active ingredient may be in the form of any conventional formulation. The chondroprotective agent may contain the present substance alone, or a mixture of the present substance with any pharmaceutically acceptable carrier or diluent. The chondroprotective agent may contain the active ingredient in an amount of 0.01 to 100 percent by weight, preferably 0.1 to 70 percent by weight.

The chondroprotective agent of the present invention may be administered orally or by some other routes.

The dose of the chondroprotective agent according to the present invention varies with the patient (animal or human), age, individual differences, state of illness, and the like. Generally speaking, however, when a human is treated, the dose of oral administration of the present substance is in the range of 0.1 to 500 mg/kg (body weight) per day, preferably 0.5 to 200 mg/kg (body weight), which is usually divided into 1 to 4 dosages in a day, although the dose outside the above range may sometimes be administered.

EXAMPLE

The present invention now will be further illustrated by, but is by no means limited to, the following Examples.

Example 1

Effect of Test Compounds on Proteoglycan Depletion in Chondrocyte Culture (a) Preparation of Cultured Chondrocytes The cartilages were sterilely extracted from the shoulder and knee joints of rabbits (New Zealand White Rabbits) (body weight of 1 to 1.5 kg). The cartilages were thoroughly washed with PBS (−) (free of $Ca^{2+}$, $Mg2+$), Hanks' solution and 0.1% EDTA-PBS (−), and then cut into small segments (1 mm×1 mm×1 mm). After PBS (−) containing 0.1% EDTA was added, the segments were allowed to stand in an incubator of 37° C. for 30 minutes. Then, the segments were treated with a trypsin solution (0.25%) at 37° C. for one hour to remove the connective tissue adhered to the cartilage. After the supernatant had been removed, the cartilages were treated for about 2 to 2.5 hours in a Ham F-12 medium containing 10% fetal bovine serum (FBS) and 0.2% collagenase. Then, the collagenase solution was centrifuged (1500 r.p.m.), and the residual chondrocytes were washed twice with a Ham F-12 medium (chondrocyte culture medium) containing 10% FBS. Finally, the resulting suspension was adjusted so that the chondrocytes were suspended in the concentration of $3 \times 10^5$ cells/ml in the chondrocyte culture medium. The chondrocytes were seeded in an amount of 1 ml/well on 24-well plates. The chondrocytes became confluent after 4 days. The experiment were performed within two weeks after reaching the confluent stage.

(b) Addition of Compounds to be tested and Proteoglycan Depleting Agents

The chondrocyte culture medium which had been used for cultivating the chondrocytes was removed from each well and 800 μl of fresh serum-free S-Clone medium containing 0.1% human serum albumin was added. Further, 100 μl of S-Clone medium containing the compounds to be tested (containing the compound in the concentration of 10 fold the final concentration; DMSO concentration=2.5%) was added. The chondrocytes were cultured in the presence of carbon dioxide (5%) and air (95%) for 2 hours. Then, the proteoglycan depleting agent, PMA (phorbol myristate acetate) (final concentration=0.1 μg/ml) was added into the culture medium of the chondrocytes.

The compounds to be tested were as follows:

Compounds of present invention: apigenin (present substance No. 5), luteolin (present substance No. 8), acacetin (present substance No. 11), linarin (present substance No. 12), diosmetin (present substance No. 13), baicalein (present substance No. 15), fisetin (present substance No. 16), kaempferol (present substance No. 17), quercetin (present substance No. 22), hesperetin (present substance No. 41, (S) isomer), and hesperidin (present substance No. 42, (S) isomer) (all from Funakoshi Co.)

Comparative substance: Indometacin (Sigma Chemical Co.) (c) Determination of proteoglycan Proteoglycan depletion was determined by the measurement of the glycosaminoglycan (major constituent of proteoglycan, hereinafter referred to as GAG) content following digestion of the chondrocyte matrix with papain.

After 2 days, the supernatant of the chondrocyte culture was removed. Then, 1 ml of 0.03% papaine solution was added to the remaining chondrocyte matrix layer and a reaction was performed at 65° C. for 1 hour to liberate the GAG from the matrix layer. The content of the GAG in the treated papaine solution was determined by the 1,9-dimethylmethylene blue method (refer to R. W. Farndale, Biochim. Biophys. Acta., Vol. 883, pp. 173 to 177, 1986). The GAG content in the chondrocyte matrix of the control test wherein the proteoglycan depleting agent was not added was shown as "100", and the relative amount of the GAG of each experiment except the control test was calculated by following formula:

GAG relative amount (%)=(B/A)×100 wherein A represents the GAG content of the control tests wherein the proteoglycan depleting agent was not added, and B represents the GAG content wherein the proteoglycan depleting agents were added alone or the GAG content wherein the proteoglycan depleting agents and the compounds to be tested were added.

The GAG contents of the control tests varied in a range of 11.23 to 59.0 μg/ml, depending on the period from the time when the chondrocytes became confluent until the time when the chondrocytes were used in the above experiment.

The results are shown in Table 2. The GAG content is the value of the mean value±standard error (n=3 to 6). For each of the compounds to be tested, the control test and the proteoglycan depleting test wherein the proteoglycan depleting agent was added were carried out and the results thereof are also shown. The significance was determined by Student's t-test with respect to the proteoglycan depleting test wherein the proteoglycan depleting agent was added. The results of the determination are shown as follows:

*: P<0.05;

\*\*: P<0.01;
\*\*\*: P<0.001.

In comparison with the GAG content in the control tests wherein the proteoglycan depleting agent was not added, the addition of the proteoglycan depleting agents, PMA, induced a loss of GAG content. Under these conditions, the present compound significantly inhibited or reduced the loss of GAG content, and showed a function to inhibit or suppress the proteoglycan depletion. On the other hand, indomethacin, a conventional analgesic and anti-inflammatory agent, did not show the function to inhibit or suppress the proteoglycan depletion, but caused a significant exacerbation on the proteoglycan depletion.

TABLE 2

| Samples | GAG content (μg/ml) | (Relative amount of GAG) (%) |
|---|---|---|
| Control | 54.7 ± .08*** | (100) |
| PMA | 16.5 ± 0.7 | (30.2) |
| PMA + No. 5 (100 μM) | 33.3 ± 0.7*** | (60.9) |
| Control | 54.8 ± 0.5*** | (100) |
| PMA | 15.2 ± 0.6 | (27.7) |
| PMA + No. 8 (100 μM) | 28.6 ± 0.5*** | (52.2) |
| PMA + No. 17 (100 μM) | 30.5 ± 0.3*** | (55.7) |
| Control | 54.0 ± 1.2*** | (100) |
| PMA | 20.0 ± 0.4 | (37.0) |
| PMA + No. 11 (100 μM) | 24.2 ± 0.3 | (44.8) |
| PMA + No. 16 (100 μM) | 30.1 ± 0.9*** | (55.7) |
| Control | 55.3 ± 0.6*** | (100) |
| PMA | 17.5 ± 0.7 | (31.6) |
| PMA + No. 12 (100 μM) | 19.8 ± 0.7* | (35.8) |
| PMA + No. 13 (100 μM) | 27.1 ± 0.7*** | (49.0) |
| Control | 11.23 ± 0.2*** | (100) |
| PMA | 4.94 ± 0.1 | (44.0) |
| PMA + No. 15 (100 μM) | 7.67 ± 0.5* | (68.3) |
| Control | 56.1 ± 0.8*** | (100) |
| PMA | 20.4 ± 0.7 | (36.4) |
| PMA + No. 22 (100 μM) | 31.0 ± 0.6*** | (55.3) |
| PMA + No. 42 (100 μM) | 24.0 ± 0.6** | (42.8) |
| Control | 59.0 ± 0.9*** | (100) |
| PMA | 21.1 ± 0.6 | (35.8) |
| PMA + No. "(100 μM) | 28.7 ± 0.4*** | (48.6) |
| Control | 28.0 ± 0.7*** | (100) |
| PMA | 15.4 ± 0.5 | (55.0) |
| PMA + indometacin | | |
| (10 μM) | 13.2 ± 0.6* | (47.1) |
| (33 μM) | 11.7 ± 0.8** | (41.8) |

Example 2

Formulation of Granule

The following ingredients were mixed homogeneously:

| | |
|---|---|
| Apigenin | 20 parts by weight |
| Lactose | 68 parts by weight |
| Low-substituted hydroxypropylcellulose | 10 parts by weight |
| Hydroxypropylcellulose | 2 parts by weight |

The mixture was kneaded using 32 parts by weight of a wetting agent, ethanol. Then, the kneaded mixture was glanulated by wet granulation and dried to obtain the granule.

As explained above, the present substance strongly inhibits proteoglycan depletion from the chondrocyte matrix and exhibits a function to protect cartilage. Further, the present substance has low toxicity. Accordingly, the present substance is very useful for the treatment of arthropathy, such as rheumatoid arthritis, osteoarthritis, periarthritis humeroscapularis, shoulder-arm-neck syndrome, lumbago, and so on.

Although the present invention has been described with reference to specific embodiments, various changes and modifications obvious to those skilled in the art are deemed to be within the spirit, scope, and concept of the invention.

We claim:

1. A method for reducing destruction of an articular cartilage in a patient suffering from arthropathy, comprising administering an effective amount of a chondroprotective agent comprising a flavonoid compound of the general formula (I):

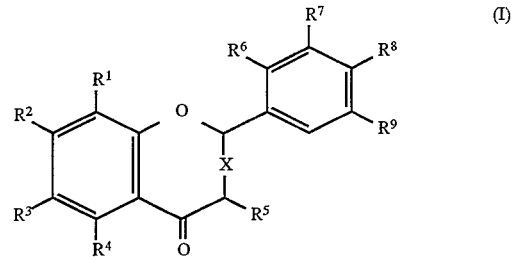

wherein $R^1$ to $R^9$ are, independently, a hydrogen atom, a hydroxyl group, or a methoxyl group and X is a double bond, or a stereoisomer thereof, and a pharmaceutically acceptable carrier, said arthropathy being rheumatoid arthritis, osteoarthritis, periarthritis humeroscapularis, shoulder-arm-neck syndrome, or lumbago.

2. A method for reducing destruction of an articular cartilage in a patient according to claim 1, wherein X is a double bond.

3. A method for reducing destruction of an articular cartilage in a patient according to claim 2, wherein said flavonoid compound is one or more compounds selected from the group consisting of flavone, chrysin, primetin, apigenin, luteolin, acacetin, diosmetin, baicalein, fisetin, kaempferol, quercetin, morin, myricetin, datiscetin, quercetagetin, rhamnetin, and isorhamnetin.

4. A method for reducing destruction of an articular cartilage in a patient according to claim 1, wherein said flavonoid compound is one or more compounds selected from the group consisting of apigenin, luteolin, acacetin, diosmetin, baicalein, fisetin, keampferol, quercetin, and hesperetin (S-form).

5. A method for reducing destruction of an articular cartilage in a patient according to claim 1, wherein said flavonoid compound or stereoisomer thereof is an extract from a naturally occurring material.

6. A method for treating arthropathy, comprising administering to a mammal in need of a chondroprotective agent an effective amount of a chondroprotective agent comprising a flavonoid compound of the general formula (I):

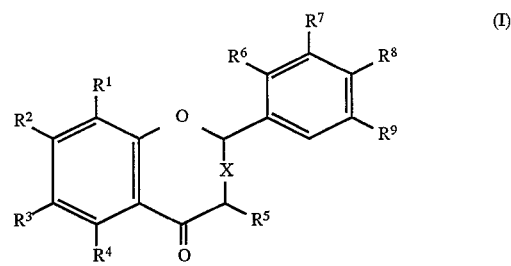

wherein $R^1$ to $R^9$ are, independently, a hydrogen atom, a hydroxyl group, or a methoxyl group and X is a double bond, or a stereoisomer thereof, and a pharmaceutically acceptable carrier, said arthropathy being rheumatoid arthritis, osteoarthritis, periarthritis humeroscapularis, shoulder-arm-neck syndrome, or lumbago.

7. A method for reducing proteoglycan depletion in an articular cartilage of a patient suffering from arthropathy, comprising administering an effective amount of chondroprotective agent comprising a flavonoid compound of the general formula (I):

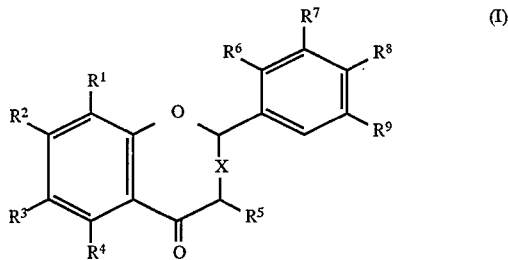

wherein $R^1$ to $R^9$ are, independently, a hydrogen atom, a hydroxyl group, or a methoxyl group and X is a double bond, or a stereoisomer thereof, and a pharmaceutically acceptable carrier, said arthropathy being rheumatoid arthritis, osteoarthritis, periarthritis humeroscapularis, shoulder-arm-neck syndrome, or lumbago.

8. A method for reducing proteoglycan depletion in an articular cartilage of a patient according to claim 7, wherein X is a double bond.

9. A method for reducing proteoglycan depletion in an articular cartilage of a patient according to claim 8, wherein said flavonoid compound is one or more compounds selected from the group consisting of flavone, chrysin, primetin, apigenin, luteolin, acacetin, diosmetin, baicalein, fisetin, kaempferol, quercetin, morin, myricetin, datiscetin, quercetagetin, rhamnetin, and isorhamnetin.

10. A method for reducing proteoglycan depletion in an articular cartilage of a patient according to claim 7, wherein said flavonoid compound is one or more compounds selected from the group consisting of apigenin, luteolin, acacetin, diosmetin, baicalein, fisetin, keampferol, quercetin, and hesperetin (S-form).

11. A method for reducing proteoglycan depletion in an articular cartilage of a patient according to claim 8, wherein said flavonoid compound or stereoisomer thereof is an extract from a naturally occurring material.

* * * * *

UNITED STATES PATENT AND TRADEMARK OFFICE
CERTIFICATE OF CORRECTION

PATENT NO.    : 5,650,433
DATED         : July 22, 1997
INVENTOR(S)   : Koju WATANABE et al It is certified that error(s) appears in the above-identified patent and that said Letters Patent is hereby corrected as shown below:

In claim 11, at column 10, line 19, change "claim 8" to --claim 7--.

Signed and Sealed this

Twenty-second Day of December, 1998

Attest:

BRUCE LEHMAN

Attesting Officer    Commissioner of Patents and Trademarks